US010271983B2

(12) United States Patent
Morris

(10) Patent No.: US 10,271,983 B2
(45) Date of Patent: Apr. 30, 2019

(54) ANKLE FOOT ORTHOPAEDIC DEVICES

(75) Inventor: Philip George Littleavon Morris, Edenbridge (GB)

(73) Assignee: C-Pro Direct, Ltd. (GB)

( * ) Notice: Subject to any disclaimer, the term of this patent is extended or adjusted under 35 U.S.C. 154(b) by 1237 days.

(21) Appl. No.: 13/884,058

(22) PCT Filed: Nov. 7, 2011

(86) PCT No.: PCT/GB2011/052157
§ 371 (c)(1),
(2), (4) Date: May 8, 2013

(87) PCT Pub. No.: WO2012/063049
PCT Pub. Date: May 18, 2012

(65) Prior Publication Data
US 2013/0226059 A1  Aug. 29, 2013

(30) Foreign Application Priority Data
Nov. 8, 2010 (GB) .................................. 1018749.0

(51) Int. Cl.
*A61F 5/00* (2006.01)
*A61F 5/01* (2006.01)

(52) U.S. Cl.
CPC .......... *A61F 5/0127* (2013.01); *A61F 5/0111* (2013.01); *A61F 2005/0162* (2013.01); *A61F 2005/0167* (2013.01)

(58) Field of Classification Search
CPC ........ A61F 5/01; A61F 5/0102; A61F 5/0127; A61F 2005/0132; A61F 2005/0134;
(Continued)

(56) References Cited

U.S. PATENT DOCUMENTS

| 589,253 A | * | 8/1897 | Engberg | ................ A61F 5/0111 |
| | | | | 280/11.36 |
| 3,086,521 A | * | 4/1963 | Desai | .................... A61F 5/0127 |
| | | | | 602/16 |

(Continued)

FOREIGN PATENT DOCUMENTS

DE   29909113   11/1999

OTHER PUBLICATIONS

International Search Report and Written Opinion dated Jul. 6, 2012, from International Application No. PCT/GB2011/052157.

*Primary Examiner* — Kari K Rodriquez
*Assistant Examiner* — Camtu T Nguyen
(74) *Attorney, Agent, or Firm* — Keusey & Associates, P.C.

(57) ABSTRACT

An ankle foot orthopaedic device (56) includes a first part (58) for association with a leg engaging item (72), a second part (60) for association with a foot engaging item (86) and a connector (62) for connecting the first part (58) to the second part (60). The connector (62) includes a first adjuster (66), which, in an adjustment condition, permits a first adjustment relative movement of the first part (58) and the second part (60) around a first device axis (150) of rotation. The connector (62) includes a second adjuster (64), which, in an adjustment condition, permits a second adjustment relative movement of the first part (58) and the second part (60) around a second device axis (144) of rotation. In use in a fitted condition in which the device (56) is fitted to a user's leg and foot, the first device axis (150) substantially corresponds with a dominant anatomical axis (50) of rotation of the sub talar joint and the second device axis (144) substantially corresponds with a dominant anatomical axis (44) of rotation of the tibio-talar joint.

17 Claims, 13 Drawing Sheets

(58) Field of Classification Search
CPC ...... A61F 2005/0151; A61F 2005/0153; A61F 2005/0179; A61F 2005/0197; A61F 2005/0137; A61F 2005/0139; A61F 2005/0141; A61F 2005/0146; A61F 2005/0148; A61F 2005/0165; A61F 2005/0167; A61F 2005/162; A61F 2005/016; A61F 5/0113; A61F 5/0111
USPC ........ 36/88, 89, 113, 115, 117.5, 117.7, 118, 36/118.3, 118.4, 118.7, 118.9, 140, 36/142–144, 160; 128/846, 869, 882; 602/5, 12, 16, 23, 27–29, 60–61, 65
See application file for complete search history.

(56) References Cited

U.S. PATENT DOCUMENTS

| | | | | |
|---|---|---|---|---|
| 5,014,690 A * | 5/1991 | Hepburn | ............... | A61F 5/0195 602/16 |
| 5,144,943 A * | 9/1992 | Luttrell | ................ | A61F 5/0111 601/33 |
| 5,215,508 A * | 6/1993 | Bastow | ................. | A63B 23/08 482/112 |
| 5,446,976 A * | 9/1995 | Donnadieu | .......... | A43B 5/0411 36/117.2 |
| 5,486,157 A * | 1/1996 | DiBenedetto | ......... | A61F 5/0127 602/16 |
| 5,542,912 A * | 8/1996 | Hess | .................... | A61F 5/0585 128/882 |
| 5,545,127 A * | 8/1996 | DeToro | ................. | A61F 5/0127 602/27 |
| 5,792,087 A * | 8/1998 | Pringle | ................. | A61F 5/0127 602/23 |
| 6,102,881 A * | 8/2000 | Quackenbush | .......... | A43B 7/20 36/140 |
| 6,267,742 B1 * | 7/2001 | Krivosha | .............. | A61F 5/0585 128/882 |
| 6,273,450 B1 * | 8/2001 | Challande | .............. | A63C 10/24 280/11.36 |
| 6,302,858 B1 * | 10/2001 | DeToro | ................. | A61F 5/0111 602/23 |
| 6,350,246 B1 * | 2/2002 | DeToro | ................. | A61F 5/0127 128/882 |
| 6,725,577 B2 * | 4/2004 | Mazzarolo | ............... | A43B 3/02 36/131 |
| 6,793,638 B1 * | 9/2004 | DeToro | ................. | A61F 5/0127 128/882 |
| 7,112,181 B1 * | 9/2006 | DeToro | ................. | A61F 5/0127 602/27 |
| 7,147,612 B2 * | 12/2006 | Molino | ................. | A61F 5/0102 128/882 |
| 7,219,450 B2 * | 5/2007 | Langley | ................... | A43B 7/20 36/10 |
| 8,062,243 B2 * | 11/2011 | DeToro | ................. | A61F 5/0127 602/16 |
| 8,425,440 B2 * | 4/2013 | DeToro | ................. | A61F 5/0127 602/12 |

* cited by examiner

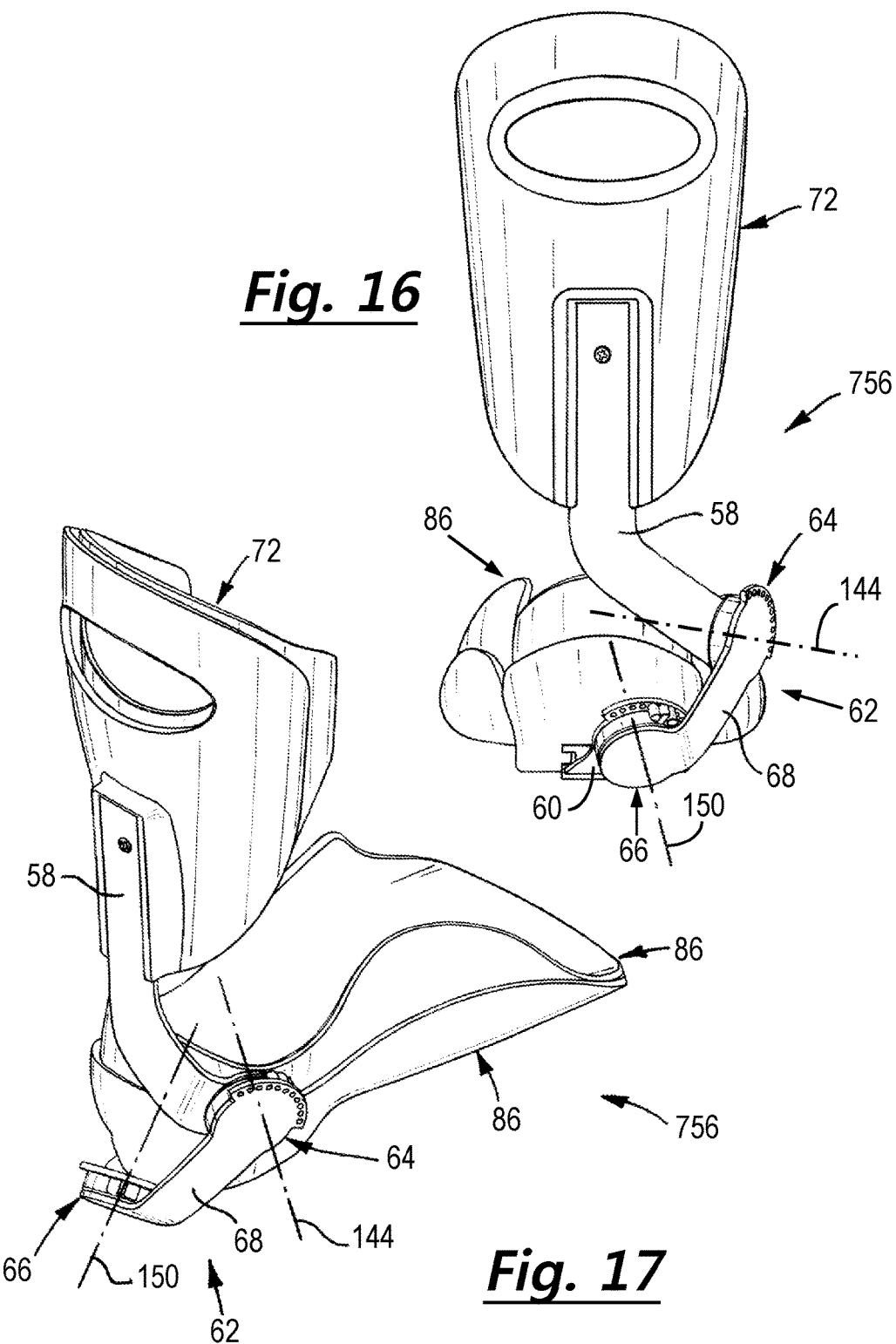

ANKLE FOOT ORTHOPAEDIC DEVICES

BACKGROUND OF THE INVENTION

1. Field of the Invention

The present invention relates to ankle foot orthopaedic devices.

2. The Prior Art

The dominant motion of the foot relative to the lower leg as required for walking and running occur through what is commonly described as the ankle joint. The ankle joint comprises two major joints each with a dominant axis of motion. The joint formed between the lower surface of the tibia and upper surface of the talus is known as the tibio-talar joint. The tibio-talar joint enables the foot to be raised and lowered or dorsiflexed and plantaflexed using medical terminology. The joint formed by the lower surface of the talus and the upper surface of the calcaneous enables the foot to be turned outwards or inwards in a rolling motion known as eversion and inversion. Anatomically correct motion of the hind foot is complex as it involves motions that are the combined motions of the motions of the tibio-talar and sub-talar joints.

People with disabling foot conditions, whether congenital, trauma related or idiopathic often benefit from therapies using orthopaedic devices or braces. Such braces typically hold the foot in a prescribed position, allow limited movement of the foot within defined constraints or bias the movement of the foot in a particular way.

Current bracing solutions cannot combine the motions of both the sub-talar and tibio talar joints meaning that in use they cannot support dynamic corrective therapies involving both sub-talar and tibio-talar joints. Current dynamic braces do not enforce anatomically correct motion of both joints.

Current bracing solutions requiring to brace or bias the sub-talar joint achieve this only through the inclusion of a connecting rigid bar between each of the user's feet or through the use of an attachment to the leg which extends well above the knee and is worn with the user's knee in a fixed and substantially bent position. Such braces are inconvenient because the user cannot walk in them and suffer from other inherent disadvantages.

Current general purpose braces to address conditions such as foot drop and many others do not provide dynamic therapy for both tibio-talar and sub-talar joints. Such braces cannot support and reinforce anatomically correct ambulation.

SUMMARY OF THE INVENTION

FIGS. 1 and 2 show part of a human lower limb 10, comprising a lower part of a leg 12, a foot 14, and an ankle joint 16 therebetween. The foot comprises a hind foot 18, amid foot 20 and a fore foot 40. FIGS. 1 and 2 also show the anatomical planes comprising the frontal plane 22, the median sagittal plane 24 and the transverse plane 36.

In this specification, standard anatomical terms are used with, for the avoidance of doubt, the meanings as set out below and by reference to FIGS. 1 and 2:

| | |
|---|---|
| Abduction | Movement in a frontal plane 22 away from median plane 24 (opposite to adduction) |
| Adduction | Movement in the frontal plane 22 towards the median plane 24 (opposite of abduction) |
| Ankle foot orthopaedic brace, device or appliance | An orthopaedic brace, device or appliance for conditions of the ankle and foot. Ankle foot orthopaedic devices may be static or dynamic. Static devices do not allow movement. Dynamic devices allow movement of the ankle and foot. |
| Ankle joint | Joint between tibia 26, fibula 28 and talus 30, which comprises tibio-talar joint 32. |
| Anterior | Front or frontward-closest to the end of the nose or toes (in human anatomy). |
| Calcaneus 38 | The heel bone (comprises the hind foot 18) |
| Dorsal | The upper side-closest to the top of the head (in human anatomy). |
| Dorsiflexion: | Rotational movement of mid foot 20 upwards in a sagittal plane 34 about the ankle joint 16. Where the angle in the sagittal plane 34 between the underside of the foot 14 and the lower leg 12 is less than 90° the foot 14 is said to be dorsiflexed beyond neutral. An angle of 75° would be referred to as 15° of dorsiflexion. |
| Eversion | A rolling movement of the mid foot 20 at sub-talar joint 42 which moves the sole away from the median plane 24 (the foot 14 rotates outwards). The opposite of inversion. |
| Frontal plane 22 | Any vertical plane that divides the body into anterior and posterior (belly and back) sections. Also known as the coronal plane. |
| Hind foot 18 | The posterior part of the foot comprising the calcaneous 38 |
| Inversion | A rolling movement of the mid foot 20 at the sub-talar joint 42 which moves the sole towards the median plane 24 (the foot 14 rotates inwards). The opposite of eversion. |
| Lateral | The side furthest from the median plane 24 of the body. |
| Medial | The side closest to the median plane 24 of the body. |
| Median plane 24 | The sagittal plane which separates the body into symmetrical halves. |
| Neutral, neutral condition | Condition in which sole of foot is substantially at 90° to the leg |
| Orthopaedic brace, device or appliance | An orthopaedic brace, device or appliance is an orthopaedic device used to control and/or guide and/or limit and/or immobilize an extremity, joint or body segment for a given reason; to restrict movement in a given direction; to assist movement more generally; to reduce weight bearing forces for a particular mobility purpose; to help with rehabilitation from fractures after the removal of a medical cast; or to otherwise correct the shape and/or function of the body to provide easier movement capability and/or reduce pain |
| Plantar | The lower side-closest to the sole of the foot (in human anatomy). |
| Plantarfiexion | Rotational movement of the mid foot 20 downwards about the ankle joint 16. When the angle in the sagittal plane 34 between the underside of the foot 14 and lower leg 12 is greater than 90° the foot 14 is said to be plantarflexed beyond neutral. An angle of 100° would be referred to as 10° of plantarflexion. |
| Posterior | Rear or rearward-furthest from the end of the nose or toes (in human anatomy). |
| Sagittal plane 34 | An imaginary plane that extends vertically from the top to the bottom of the body, dividing it into left and right portions. |
| Sub-talar joint 42 | The joint between the plantar surface of the talus 30 and the dorsal surface of the calcaneous 38. |
| Tibio-talar joint 32 | The joint between the plantar surfaces of the tibia 26 and the fibula 28, and the dorsal surface of the talus 30. |

-continued

| | |
|---|---|
| Transverse plane 36 | An imaginary plane that divides the body into superior (upper) and inferior (lower) parts, perpendicular to the frontal and sagittal planes (also known as the horizontal plane, axial plane, or transaxial plane). |
| Valgus (heel valgus) | Eversion and abduction of the calcaneus 38. |
| Varus (heel varus) | Inversion and adduction of the calcaneus 38. |

The dominant motion of the foot relative to the lower leg as required for walking and running occur through what is commonly described as the ankle joint. The ankle joint comprises two major joints each with a dominant axis of motion. The joint formed between the lower surface of the tibia and upper surface of the talus is known as the tibio-talar joint. The tibio-talar joint enables the foot to be raised and lowered or dorsiflexed and plantaflexed using medical terminology. The joint formed by the lower surface of the talus and the upper surface of the calcaneous enables the foot to be turned outwards or inwards in a rolling motion known as eversion and inversion. Anatomically correct motion of the hind foot is complex as it involves motions that are the combined motions of the motions of the tibio-talar and sub-talar joints.

People with disabling foot conditions, whether congenital, trauma related or idiopathic often benefit from therapies using orthopaedic devices or braces. Such braces typically hold the foot in a prescribed position, allow limited movement of the foot within defined constraints or bias the movement of the foot in a particular way.

This invention overcomes substantial limitations in current bracing solutions.

Current bracing solutions cannot combine the motions of both the sub-talar and tibio talar joints meaning that in use they cannot support dynamic corrective therapies involving both sub-talar and tibio-talar joints. Current dynamic braces do not enforce anatomically correct motion of both joints.

Current bracing solutions requiring to brace or bias the sub-talar joint achieve this only through the inclusion of a connecting rigid bar between each of the user's feet or through the use of an attachment to the leg which extends well above the knee and is worn with the user's knee in a fixed and substantially bent position. Such braces are inconvenient because the user cannot walk in them and suffer from other inherent disadvantages.

Current general purpose braces to address conditions such as foot drop and many others do not provide dynamic therapy for both tibio-talar and sub-talar joints. Such braces cannot support and reinforce anatomically correct ambulation.

This invention overcomes fundamental limitations of current bracing solutions and makes new improved therapies possible for people affected by a myriad of disabling conditions of the foot. The inventor has precisely understood the dominant anatomical motions of both tibio-talar and sub-talar joints and realised how to model these in a single wearable device. Of particular significance is the inventor's realisation of the significance of the surprising nature of the sub-talar joint. The invention exploits the geometry of this motion to create a dynamic orthopaedic device that can brace or bias the sub-talar joint without the need for connecting bars or a fixed and bent knee.

According to a first aspect of the present invention, there is provided an ankle foot orthopaedic device, the device including a first part for association with a leg engaging item, a second part for association with a foot engaging item, a connector for connecting the first part to the second part, the device being arrangeable in an adjustment condition in which the connector permits adjustment movement of one of the parts relative to the other of the parts, the device being arranged so that in use in a fitted condition, the adjustment movement substantially corresponds with an anatomical movement of one part of the leg and foot relative to another part of the leg and foot.

Possibly, the anatomical movement comprises movement of one leg/foot part relative to the other leg/foot part around an anatomical axis of rotation. Possibly, the adjustment movement comprises movement of the one part relative to the other part around a device axis of rotation. Possibly, in the fitted condition in which the orthopaedic device is fitted to a user's lower limb, the device axis of rotation of the adjustment movement is substantially aligned with the anatomical axis of rotation of the anatomical movement.

Possibly, the connector includes an adjuster, which, in the adjustment condition, permits the adjustment movement.

In one embodiment the connector includes a first adjuster, which may, in the adjustment condition, permit a first adjustment movement.

In another embodiment, the connector includes a second adjuster, which may, in the adjustment condition, permit a second adjustment movement.

According to a second aspect of the present invention, there is provided an ankle foot orthopaedic device, the device including a first part for association with a leg engaging item, a second part for association with a foot engaging item, a connector for connecting the first part to the second part, the connector including a first adjuster, which, in an adjustment condition, permits a first adjustment relative movement of the first part and the second part around a first device axis of rotation, the connector including a second adjuster, which, in an adjustment condition, permits a second adjustment relative movement of the first part and the second part around a second device axis of rotation, wherein, in use in a fitted condition in which the device is fitted to a user's leg and foot, the first device axis substantially corresponds with a dominant anatomical axis of rotation of the sub talar joint and the second device axis substantially corresponds with a dominant anatomical axis of rotation of the tibio-talar joint.

The device thereby models and controls anatomically correct movement of the user's foot and ankle with respect to the leg and enabling the user's sub-talar joint to be braced or biased in a position where the foot is either abducted or adducted and thereby enabling the user's tibio-talar joint to be braced or biased in a position of dorsiflexion or plantaflexion.

The device is able to brace or bias the user's foot in a position of abduction or adduction through the axis of rotation of the sub-talar joint without the need for either a connecting bar between each leg or a leg engaging item that extends above the knee joint of the leg and which requires the leg to be held in a fixed position substantially bent at the knee.

Possibly, the device axis of rotation of the first adjustment movement is, in the fitted condition, substantially aligned with an anatomical axis of relative rotation of the talus bone and the calcaneous bones at the sub-talar joint.

Possibly, the device axis of rotation of the second adjustment movement is, in the fitted condition, substantially aligned with an anatomical axis of relative rotation of the talus bone and the tibia and fibula bones at the tibio-talar joint.

Possibly, the first and second device axes are substantially aligned along the sub-talar joint axis and the tibio-talar joint axis respectively.

Possibly, the device axis of rotation of the first adjustment movement extends posterior plantar to anterior dorsal in the sagittal plane, and may subtend a first device angle to the transverse plane in the sagittal plane, and may extend posterior lateral to anterior medial in the transverse plane, and may subtend a second device angle to the sagittal plane in the transverse plane.

In a neutral condition, the first device angle may lie in the range 32° to 52°, more desirably may lie in the range 37° to 47°, and optimally may be 42°. The second device angle may lie in the range 8° to 24°, and more desirably may lie in the range 12° to 20°, and optimally may be 16°.

Possibly, the device axis of rotation of the second adjustment movement extends medial anterior to lateral posterior in the transverse plane, and may subtend a third device angle to the frontal plane in the transverse plane, and may extend medial dorsal to lateral plantar in the frontal plane, and may subtend a fourth device angle to the transverse plane in the frontal plane.

In a neutral condition, the third device angle may lie in the range 15° to 30 35°, and more desirably may lie in the range 20° to 30°, and optimally may be 25°. The fourth device angle may lie in the range 3° to 13°, and more desirably may lie in the range 6° to 10°, and optimally may be 8°.

A device according to claim 1 or 2, in which the first adjuster includes first biasing means for providing a first bracing force for bracing, in use, a user's sub talar joint in an abducted, neutral or adducted position.

Possibly, the device is moveable to a fitted, braced condition, in which the user's toot is held in any one or any suitable combination of a neutral position, an abducted position, an adducted position, a dorsiflexed position and/or a plantarflexed position, without the need for a connecting bar extending between the user's feet, or the leg engaging item extending above the user's knee, or the user's leg being held in a bent position.

Possibly, the orthopaedic device is moveable from the adjustment condition to a restricted condition, in which the adjustment movement is restricted relative to the movement permitted in the adjustment condition, or in which the adjustment movement is substantially prevented. Possibly, the or each or any one adjuster includes a restrictor, which may, in the restricted condition, restrict or substantially prevent the adjustment movement thereof. The restrictor may include limit stops, which may limit the adjustment movement thereof.

Possibly, any or each adjuster includes a bias member, which may bias the adjustment movement thereof in one direction. The bias member may apply a torsion force to bias the adjustment movement thereof in a given direction.

Possibly, the first adjuster includes first biasing means for providing a first bracing force for bracing, in use, a user's sub talar joint in an abducted, neutral or adducted position. Possibly, the first bracing force is a torsion force. Possibly, the first biasing means includes a first bias member.

Possibly, the second adjuster includes second biasing means for providing a second bracing force for bracing, in use, a user's tibio talar joint in a dorsiflexed, neutral or plantarflexed position. Possibly, the second bracing force is a torsion force. Possibly, the second biasing means includes a second bias member.

Possibly, the first adjuster includes first biasing means for providing a first bracing force and the second adjuster includes second biasing means for providing a second bracing force which, in use, together and simultaneously brace the user's foot in any one or any suitable combination of a neutral position, an abducted position, an adducted position, a dorsiflexed position and/or a plantarflexed position.

Possibly, the or each or any one adjuster includes an indicator, which may indicate a relative degree of the adjustment movement thereof.

Possibly, the ankle foot orthopaedic device includes the leg engaging item which comprises a brace part, in which a leg part of the lower limb may be receivable. Possibly, the leg engaging item is adjustable so that in an adjusted and fitted condition it applies bracing forces through the axis of motion of each adjuster. Possibly, the bracing force when in a fitted and adjusted condition runs through the centre point of the leg section where the leg engaging item engages with the leg at an angle which is perpendicular to the device axis of rotation of the first adjuster. Possibly, the bracing force when in a fitted and adjusted condition runs through the centre point of the leg section where the leg engaging item engages with the leg at an angle which is perpendicular to the device axis of rotation of the second adjuster. Possibly, a combination of bracing forces when in a fitted and adjusted condition run through the centre point of the leg section where the leg engaging item engages with the leg at an angle which is perpendicular to the device axis of rotation of the first adjuster and where the leg engaging item engages with the leg at an angle which is perpendicular to the device axis of rotation of the second adjuster. Possibly, the direction and orientation of the bracing forces mean that when in a fitted and adjusted condition the device will maintain the position of the foot such that it is abducted or adducted about the dominant anatomical axis of motion of user's sub-talar joint and such that it is dorsiflexed or plantaflexed about the dominant anatomical axis of motion of user's tibio-talar joint.

Possibly, the ankle foot orthopaedic device includes a mounting for attaching the leg engaging item to the first connecting arm. The mounting may be adjustable to permit adjustment to fit the user's leg and to achieve the desired orientation of bracing forces relative to the axis of motion of the first and second adjusters.

Possibly, the device includes the foot engaging item, which may comprise a shoe or footplate, in which a foot part of the lower limb may be receivable.

Possibly the second connecting arm includes an attachment mechanism for attaching a foot engaging item to the device.

According to a third aspect of the present invention, there is provided a method of bracing a lower leg relative to a foot such that a connecting bar between the lower limbs is not required, a leg engaging item does not need to extend above the user's knee, or the user's leg does not need to be held in a bent position, the method including providing an ankle foot orthopaedic device according to any of the preceding statements.

According to a fourth aspect of the present invention, there is provided a splint for aiding immobilisation of a body part including an ankle foot orthopaedic device according to any of said preceding statements.

According to a fourth aspect of the present invention, there is provided an ankle foot orthopaedic device, the device including a first part for association with a leg engaging item, a second part for association with a foot engaging item, a connector for connecting the first part to the second part, the connector including an adjuster, which, in an adjustment condition, permits an adjustment relative movement of the first part and the second part around a device axis of rotation, the adjuster including biasing means for providing a torsion force.

Possibly, the biasing means include a bias member.

BRIEF DESCRIPTION OF THE DRAWINGS

Embodiments of the present invention will now be described, by way of example only, and with reference to the accompanying drawings, in which:~

FIG. 16 is a rear view of an sixth orthopaedic device;

FIG. 17 is a perspective lateral side view of the orthopaedic device of FIG. 20.

Figure 1:
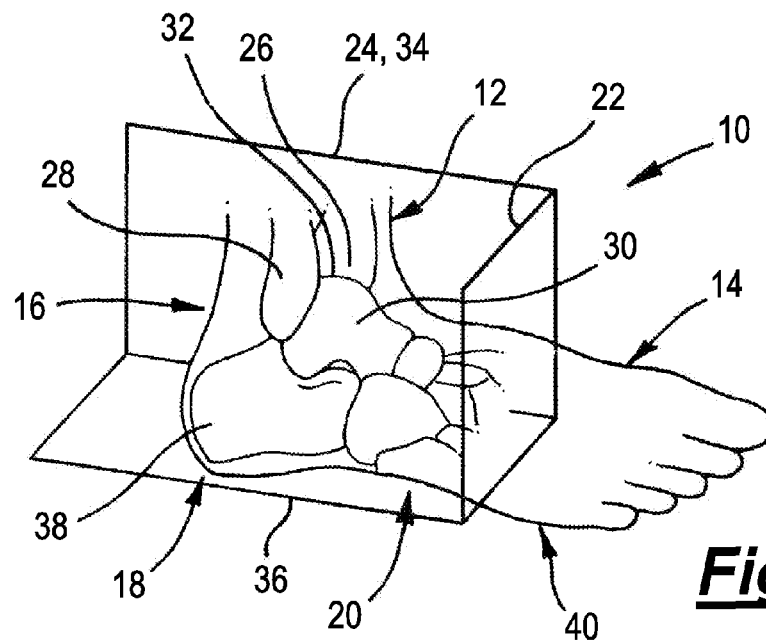
FIG. 1 is a perspective lateral view of a human right foot showing the bones of the ankle joint and hind foot and the anatomical planes.
Figure 2:
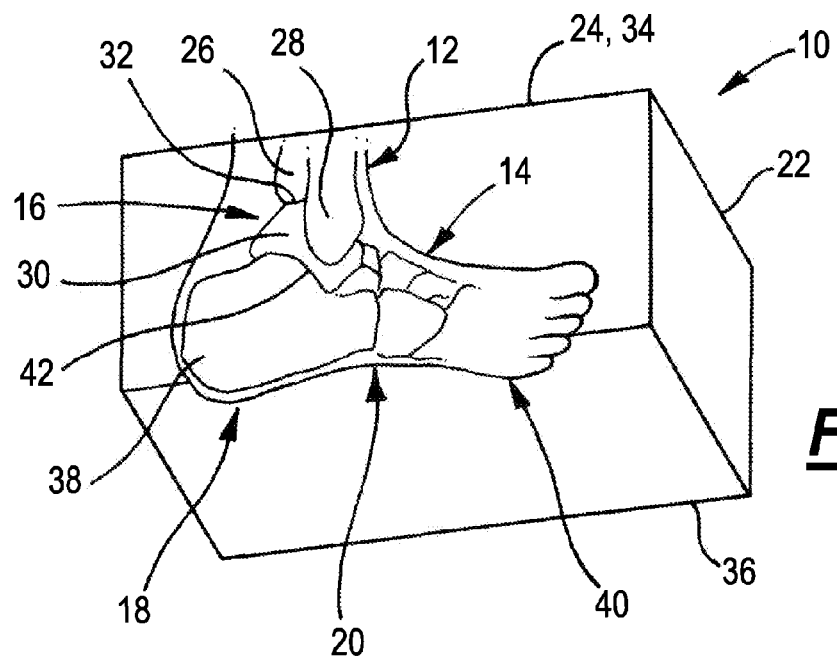
FIG. 2 is a perspective rear and lateral view of the foot and planes of FIG. 1.
Figure 3A:
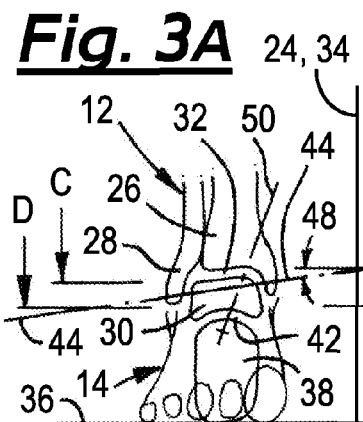
FIGS. 3A to 3D are simplified diagrammatic cross sectional views of a human right foot through the tibio-talar and sub-talar joints, FIG. 3A being a front (anterior) view, FIG. 3B being an exterior side (lateral) view, FIG. 3C being a plan (dorsal) view at the level of the tibio-talar joint as indicated by the line C-C in FIG. 3A and FIG. 3D being a plan (dorsal) view at the level of the sub-talar joint as indicated by the line D-D in FIG. 3A.
Figure 3B:
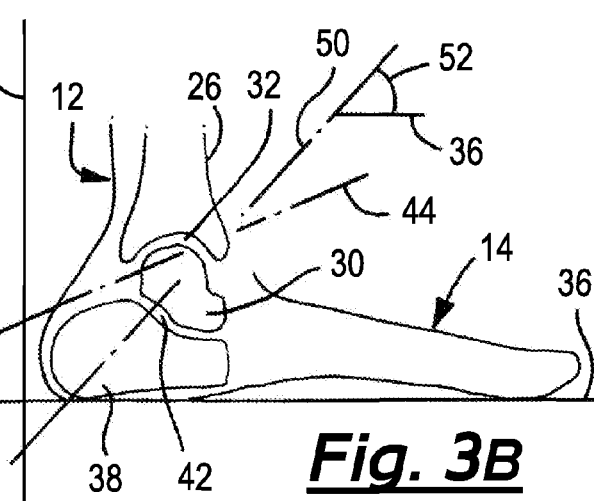
Figure 3C:
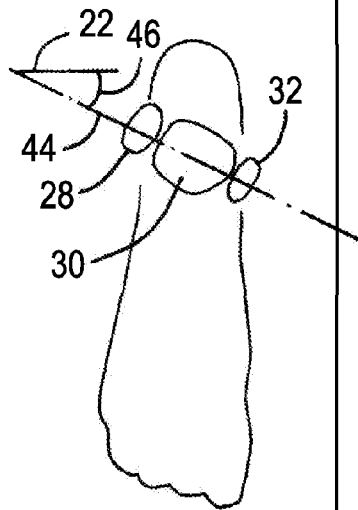
Figure 3D:
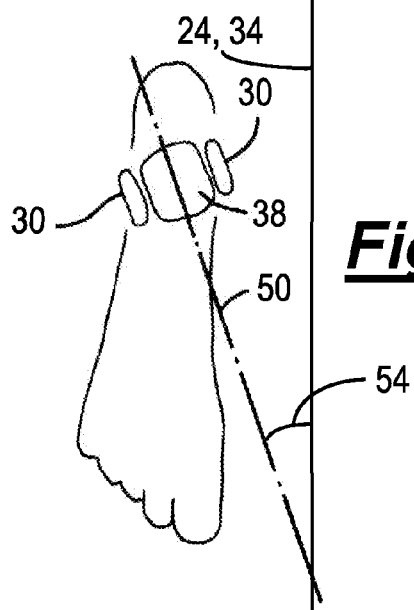

Save for FIGS. 4A, 4B, 4C and 4D the devices shown are all for the left lower limb. The skilled person will appreciate that devices for the right lower limb will be symmetrical.

DETAILED DESCRIPTION OF THE PREFERRED EMBODIMENTS

The movement of the foot 14 relative to the leg 12 is relatively complex. The surfaces which comprise the tibiotalar and sub-talar joints permit three dimensional movement which has been found to be difficult to describe, analyse and model adequately. The movement can be irregular and can vary between individuals. Thus, for example, the tibio-talar joint has been described in various different studies as having a helical axis; as having a hinge axis; and as having multiple axes which are different during plantarflexion and dorsiflexion.

The applicant has realised that for the purposes of providing an orthopaedic device for the treatment of various conditions of the ankle and foot, the movement of the foot 15 relative to the leg 12 can be simplified and yet accurately modelled as shown in FIGS. 3A to 3D.

In this analysis and modelling, the movement at the sub-talar joint 42 is simplified as being rotational around a sub-talar pivot axis 50 which extends posterior plantar to anterior dorsal in the sagittal plane 34, subtending a first anatomical angle 52 to the transverse plane 36 in the sagittal plane 34, and extends posterior lateral to anterior medial in the transverse plane 36, subtending a second anatomical angle 54 to the sagittal plane 34 in the transverse plane 36.

With the foot 14 in the neutral condition, the first anatomical angle 52 can lie in the range 32° to 52°, and more frequently lies in the range 37° to 47°, and usually is approximately 42°. In the neutral condition, the second anatomical angle can lie in the range 8° to 24°, and more frequently lies in the range 12° to 20°, and usually is approximately 16°.

In this analysis and modelling, the movement at the tibio-talar joint 32 is simplified as being rotational around a tibio-talar pivot axis 44 which extends medial anterior to lateral posterior in the transverse plane 36, subtending a third anatomical angle 46 to the frontal plane 22 in the transverse plane 36, and extends medial dorsal to lateral plantar in the frontal plane 22, subtending a fourth anatomical angle 48 to the transverse plane 36 in the frontal plane 22.

With the foot 14 in the neutral condition as shown in FIGS. 3A to 3D, the third anatomical angle 46 can lie in the range 15° to 35°, and more frequently lies in the range 20° to 30°, and usually is approximately 25°. In the neutral condition, the fourth anatomical angle 48 can lie in the range 3° to 13°, and more frequently lies in the range 6° to 10°, and usually is approximately 8°.

Broadly and approximately, the anatomical movement at the tibio-talar joint 32 can be regarded as plantarflexion or dorsiflexion, and the anatomical movement at the sub-talar joint 42 can be regarded as a combination in equal parts of abduction and eversion or a combination in equal parts of adduction and inversion.

FIGS. 4 to 9 show an ankle foot orthopaedic device 56, the design of which is based on the analysis and modelling described above.

The device 56 includes a first part in the form of a first connecting arm 58 for association with a leg engaging item 72, a second part in the form of a shoe engaging item 60 for association with a foot engaging item 86 and a connector 62 for connecting the first connecting arm 58 to the shoe engaging item 60. The connector 62 includes a first adjuster 66, which, in an adjustment condition, permits a first adjustment relative movement of the first connecting arm 58 and the shoe engaging item 60 around a first device axis 150 of rotation. The connector 62 includes a second adjuster 64, which, in an adjustment condition, permits a second adjustment relative movement of the first connecting arm 58 and the shoe engaging item 60 around a second device axis 144 of rotation. In use in a fitted condition in which the device 56 is fitted to a user's leg and foot, the first device axis 150 substantially corresponds with a dominant anatomical axis of rotation of the sub talar joint 50 and the second device axis 144 substantially corresponds with a dominant anatomical axis 44 of rotation of the tibio-talar joint.

By the term "foot engaging item" the skilled person will understand that the item concerned could engage a bare foot, a clothed foot, or an item of footwear such as a shoe or a boot. Similarly, by the term "shoe engaging item" the skilled person will understand that the item concerned could engage any suitable item of footwear such as a footplate, a shoe or a boot.

The connector 62 includes a second connecting arm 68 which extends between and spaces apart the first and second adjusters 66, 64.

In the adjustment condition the first adjuster 66 permits a first rotational adjustment movement around a first device axis of rotation 150 of the second connecting arm 68 relative to the shoe engaging item 60. In the adjustment condition the second adjuster 64 permits a second rotational adjustment movement around a second device axis of rotation 144 of the second connecting arm 68 relative to the first connecting arm 58.

The first connecting arm 58 and the second connecting arm 68 need to be formed to correctly position the first adjuster 66 and second adjuster 64 with respect to the user and to achieve the correct alignment of the first device axis of rotation 150 and the second device axis of rotation 144. Both connecting arms need to be manufactured from a rigid, but lightweight material such as 30% glass filled nylon. Both adjusters need to create a rigid yet smooth running axis of motion capable of withstanding significant torsion forces required to brace or bias the users foot. Both adjusters might be made from a steel spigot running in a nylon sleeve. The device may be produced from any suitable materials providing there is sufficient rigidity and the adjusters run freely under load.

Figure 5:
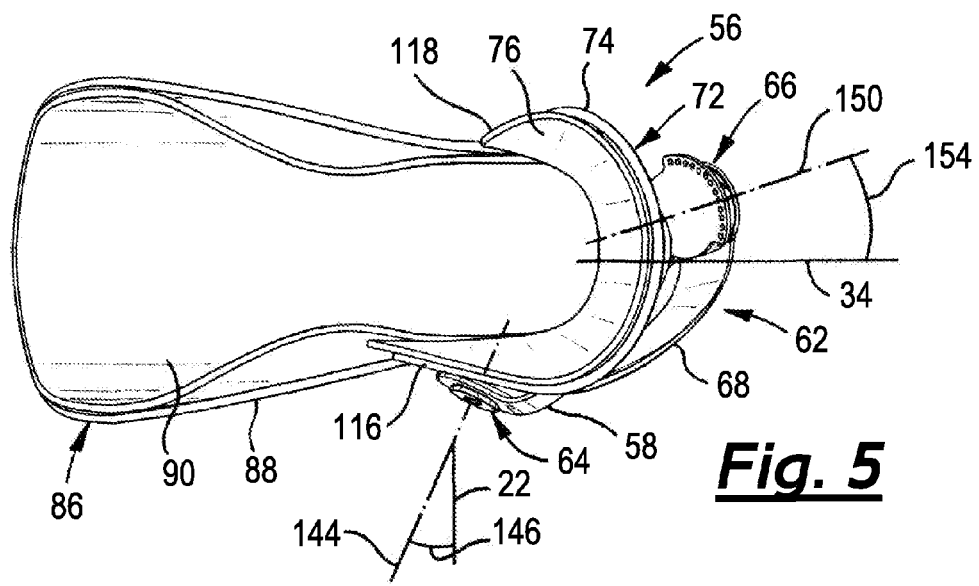
FIG. 5 is a plan view of the orthopaedic device of FIG. 4.
Figure 6:
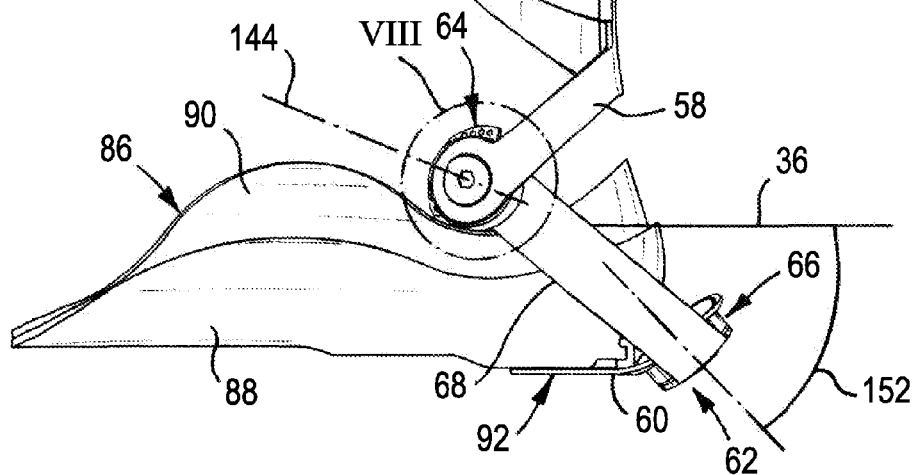
FIG. 6 is a lateral side view of the orthopaedic device of FIGS. 4 and 5.
Figure 7:
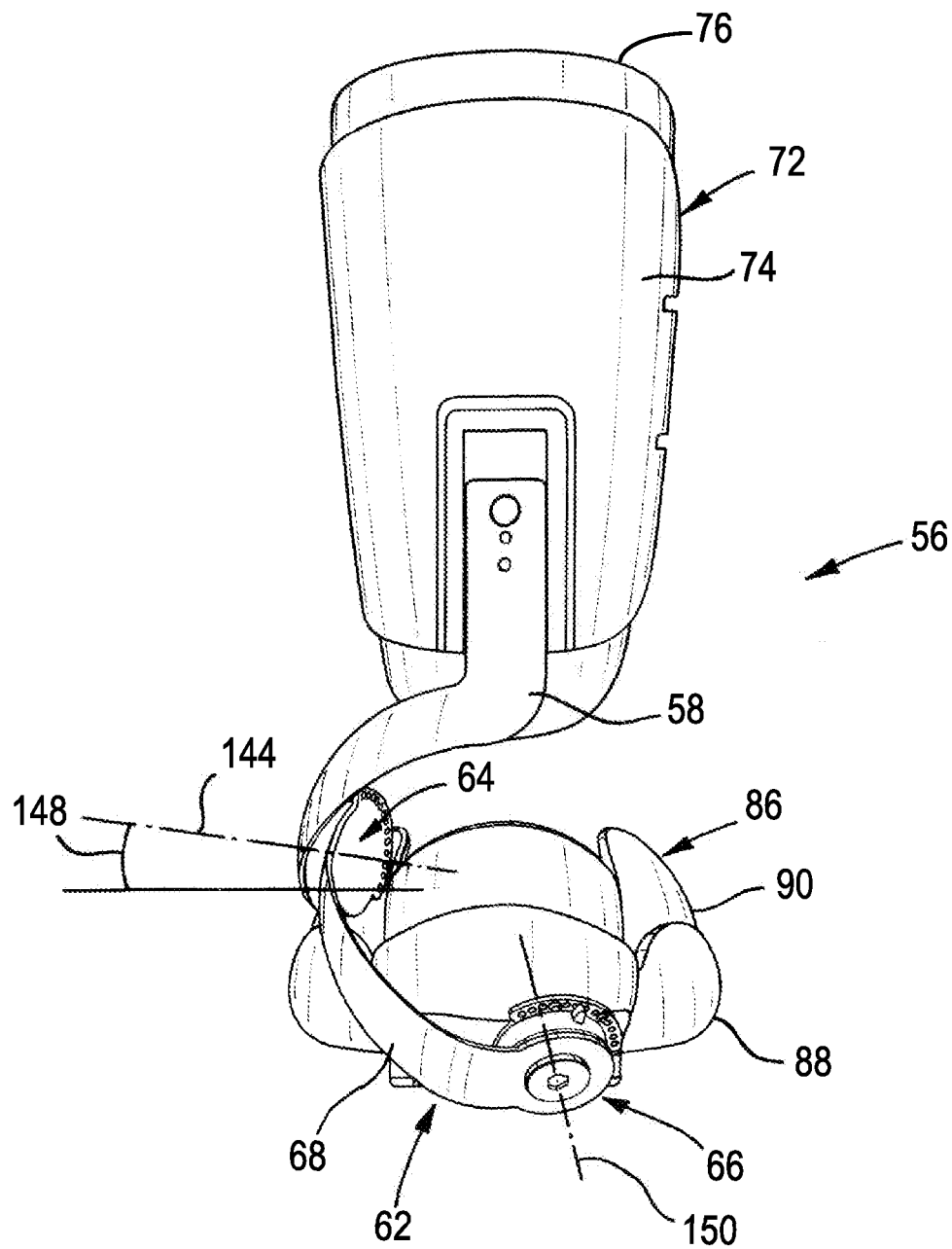
FIG. 7 is a rear view of the orthopaedic device of FIGS. 4 to 6.

Referring specifically to FIGS. 5 to 7:

The first device axis 150 of rotation of the first adjuster 66 subtends a first device angle 152 to the transverse plane 36 in the sagittal plane 34 extending posterior plantar to anterior dorsal, and subtends a second device angle 154 to the sagittal plane 34 in the transverse plane 36 extending posterior lateral to anterior medial.

In one example, in the neutral condition, the first device angle 152 could be 42°. In other examples, in the neutral condition, the first device angle 152 could lie in the range 32° to 52°, and more desirably could lie in the range 37° to 47°.

In one example, in the neutral condition, the second device angle 154 could be 16°. In other examples, in the neutral condition, the second device angle 154 could lie in the range 8° to 24°, and more desirably could lie in the range 12° to 20°.

The second device axis 144 of rotation of the second adjuster 64 subtends a third device angle 146 to the frontal plane 22 in the transverse plane 36 extending medial anterior to lateral posterior, and subtends a fourth device angle 148 to the transverse plane 36 in the frontal plane 22 extending medial dorsal to lateral plantar.

In one example, in the neutral condition, the third device angle 146 could be 25°. In other examples, the third device angle 146 could lie in the range 15° to 35°, and more desirably could lie in the range 20° to 30°.

In one example, in the neutral condition, the fourth device angle 148 could be 8°. In other examples, the fourth device angle 148 could lie in the range 3° to 13°, and more desirably could lie in the range 6° to 10°.

In the example shown in FIGS. 4 to 9, the foot engaging item 86 is in the form of a specialised shoe, in which a part of the foot 14 is receivable in use. The shoe 86 comprises an outer relatively rigid shoe member 88 and an inner, relatively flexible cushion or pad member 90.

The shoe engaging item 60 may attach directly to a suitable shoe or to some form of shoe mounting 92 for mounting the shoe engaging item 60 and the shoe 86 together. The mounting could permit linear adjustment of the shoe 86 relative to the shoe engaging item 60.

Figure 8:
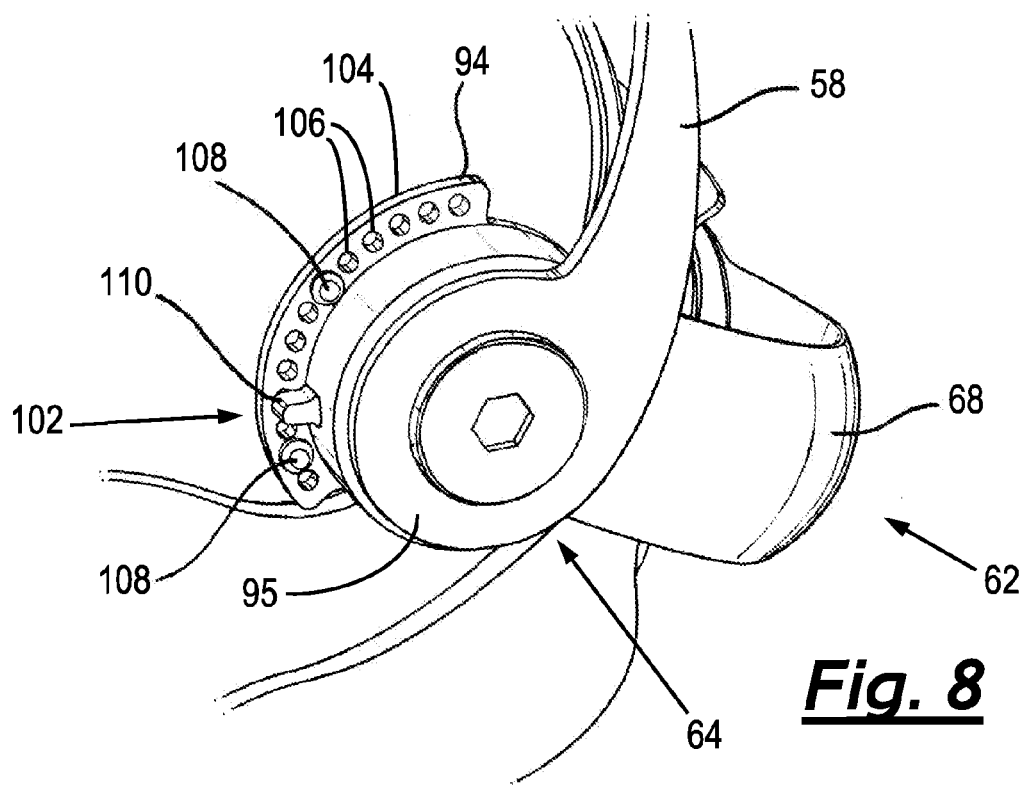
FIG. 8 is a lateral side view of a detail as indicated by the reference VIII in FIG. 6.
Figure 9:
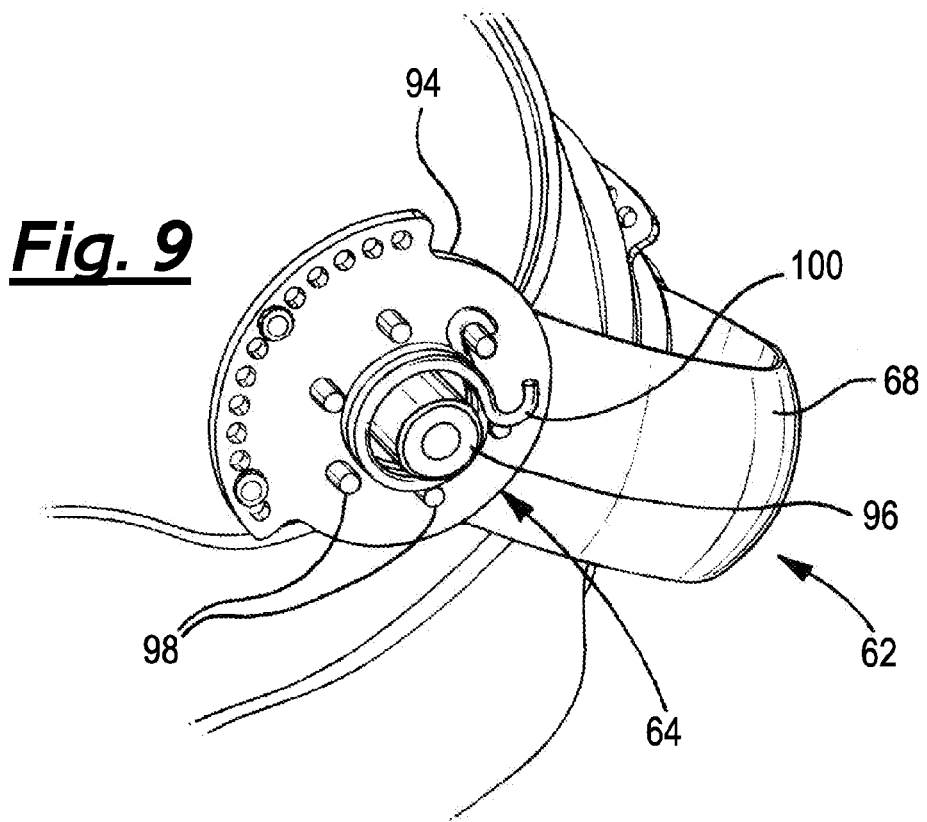
FIG. 9 is a view of the detail shown in FIG. 8, partially disassembled.

FIGS. 8 and 9 illustrate a second adjuster 64. The second adjuster 64 is formed by the union of a disc-like adjuster member 94 attached or moulded to the second connecting arm 68 from which an axle 96 extends and a cap-like adjuster member 95 which has a central hole to form a bearing contact with the axle 96. When assembled the axle 96 of the disc-like adjuster member 94 fits into the hole of the cap-like adjuster member 95 to achieve an adjustment movement in the required axis of motion. The second adjuster 64 must be manufactured to provide a movement that is both smooth running and rigid even when subject to bracing loads in use.

Pegs 98 project from the disc-like adjuster member 94. The second adjuster 64 includes second biasing means comprising a second bias member 100 in the form of a torsion spring engages one of the pegs 98 and a peg or hole in located in the internal side of the cap-like adjuster member 95. In one example, each adjuster member 94 has six equispaced pegs 98 to enable adjustment of the pre-loaded torsion forces applied by the spring in the neutral position. The second bias member 100 and pre-loaded torsion mean that the second adjuster exerts a force which either dorsiflexes or plantaflexes the shoe engaging 60 item relative to the leg engaging item 72 depending on the direction of the torsion force exerted by the bias member 100.

The configuration of the first adjuster 66 is similar to that of the second adjuster 64 except that the disc-like adjuster member 94 is attached to the shoe engaging item 60 and the cap-like adjuster member 95 is attached or moulded to the second connecting arm 68. The first adjuster 66 includes first biasing means including a first bias member 100. For the first adjuster 66 the bias member 100 and pre-loaded torsion mean that the first adjuster exerts a force which either abducts or adducts the shoe engaging item 60 relative to the leg engaging item 72 depending on the direction of the torsion force exerted by the bias member 100.

Each adjuster 64, 66 includes a restrictor 102 which includes a tab 104 which projects from, or forms part of, part of the periphery of one of the adjuster members 94 and defines a plurality of limit holes 106. The restrictor 102 includes a pair of limit stops 108 in the form of screws which are located in two of the limit holes 106. The limit stops 108 are removable and repositionable. The restrictor 102 includes a lug 110 which projects from the other of the adjustment members 94 and locates between the limit stops 108. In use, the engagement of the lug 110 with the limit stops 108 limits the respective adjustment movement.

The restrictors 102, and in particular, the positions of the limit stops 108 in the limit holes 106, determine the maximum extent of relative movement of the first connecting arm 58 and second connecting arm 68 for the second adjuster 64 and the second connecting arm 68 and shoe engaging item 60 for the first adjuster 66. In one example, the tab 104 defines twenty four limit holes 106, which are at 5° intervals. In one example, the restrictor 102 of the first adjuster 64 could be arranged to permit up to 90° of plantarflexion and up to 30° of dorsiflexion. In one example, the restrictor 102 of the second adjuster 66 could be arranged to permit up to 60° of inversion/adduction and 60° of eversion/abduction.

In the example shown in FIGS. 4 to 9, the device 56 includes the leg engaging item 72 into which a part of the leg 12 is receivable in use. The leg engaging item 72 comprises an outer relatively rigid member 74 and an inner relatively soft and flexible member 76 to provide a comfortable contact with the user's leg.

In use it is important to position the leg engaging item such that it correctly acts as a foot brace capable of simultaneously bracing or biasing both major joints of the foot. This means the sub-talar joint 42 is rotated such that the foot is either adducted or abducted and the tibio-talar joint 32 is rotated such that the foot is either dorsiflexed or plantaflexed.

Figure 4:
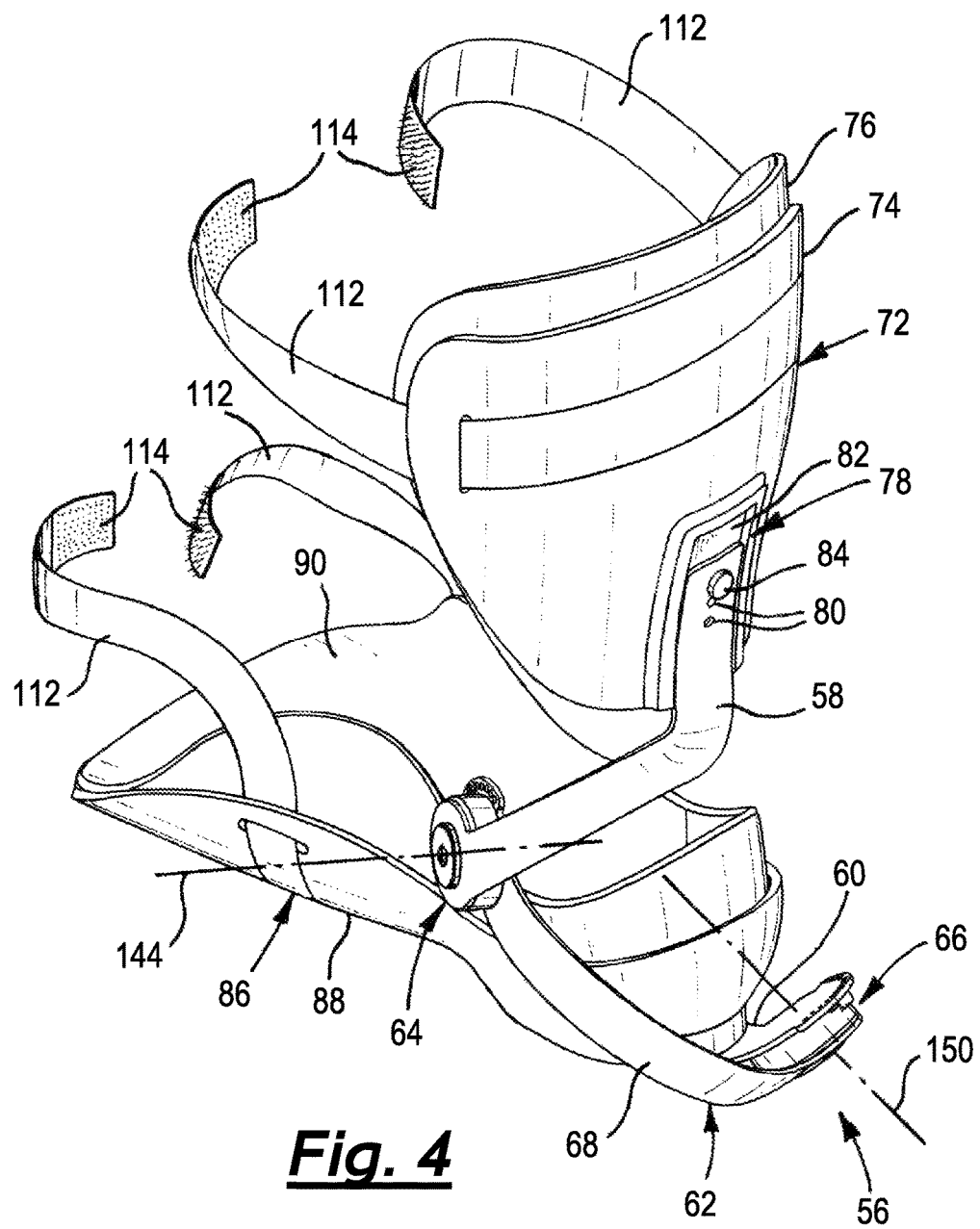
FIG. 4 is a perspective lateral side view of a first ankle foot orthopaedic device.

FIG. 4 illustrates a leg attachment 72 extending further forward on the medial side 116 than the outer lateral side 118. The example shown in FIG. 4 has the first connecting arm 58 at the rear of the device and extends the medial side 116 of the leg attachment 72, but a number of alternative configurations will achieve the required function provided that the first and second connecting arms 58, 62 and the first and second adjusters 66, 64 are sufficiently rigid and permit rotational movement only along the axes previously described.

An important feature of the device 56 is that it enables the sub-talar joint to be braced and or biased without the need for a connecting bar between the left and right feet or for a leg attachment extending above the knee and for the user's knee to be held in a substantially bent condition. FIGS. 4A, 4B, 4C and 4D illustrate how this is achieved and example configurations of the first connecting arm 58 and leg attachment 72.

Figure 4A:
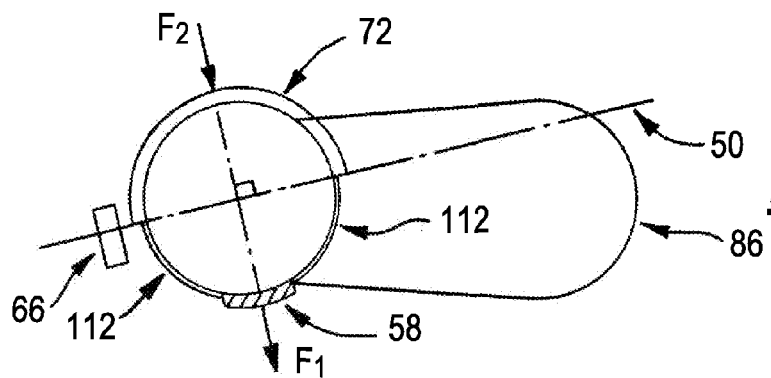
FIGS. 4A, 4B and 4C are simplified plan views of a right leg and foot illustrating how a leg attachment and first adjusters of the device of FIG. 4 interact to create a device capable of adducting or abducting the foot without the need for a connecting bar between each foot or for the user's knee to be held in a fixed and bent condition.

FIG. 4A is a simplified plan view of the device 56 in use with a suitable shoe 86, the shoe 86 is closely fitting yet allows full and free movement of both sub-talar and tibio-talar joints. Providing the leg 12 is stabilised movement of the shoe 86 will correspond to movement of the foot 14. The arrangement of the first and second adjusters 66, 64 and first and second connecting arms 58, 68 means the foot may move only according to the dominant anatomical axes of the sub-talar joint 50 and tibio-talar joint 44.

Figure 4B:
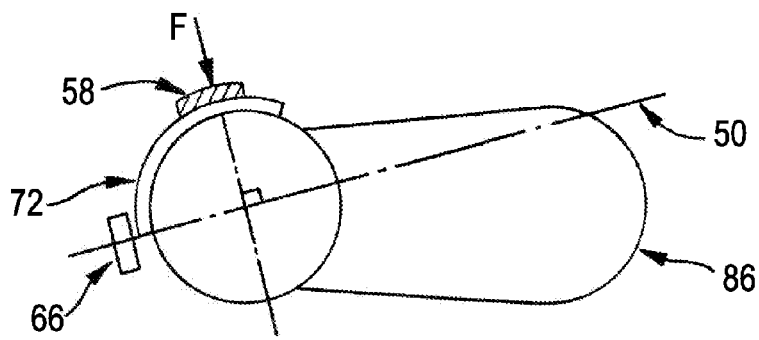
Figure 4C:
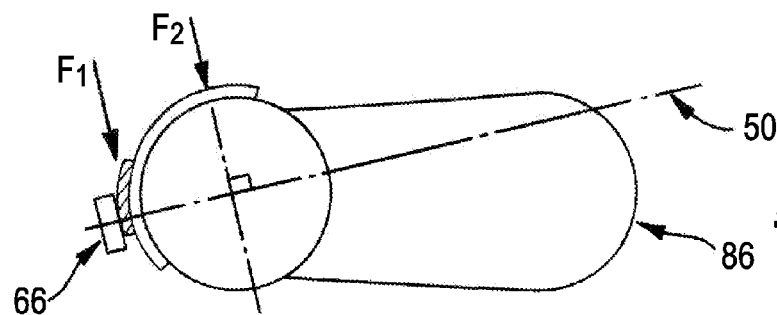
Figure 4D:
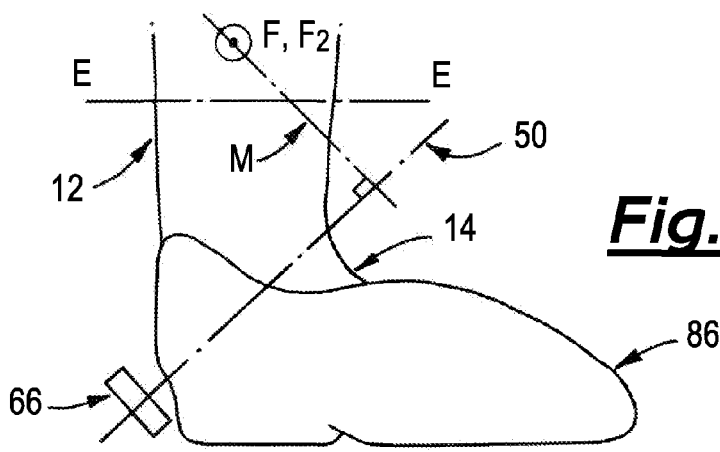
FIG. 4D is a side view of the leg, foot and device of FIGS. 4A, 4B and 4C.

In FIG. 4A the leg 12 is sectioned along the axis EE as illustrated in FIG. 4D. FIG. 4A illustrates a right foot. The first connecting arm 58 is positioned laterally. In this example the first adjuster 66 is subject to a torsion force due to the effect of the bias member 100. The effect of the torsion force is to subject the first connecting arm 58 to a force F1. The first connecting arm 58 is attached to straps 112, which in turn are connected to the leg attachment 72. The force F1 is transferred to the leg attachment such that it exerts a first bracing force F2 on the leg 12. The position of the force F2 is further illustrated in FIG. 4D where it can be seen that a turning moment M is applied through the axis of the sub-talar joint 50. Since the leg attachment 72 cannot move and acts as a brace stabilising the leg 12 relative to the foot 14, the net effect is that the shoe 86 and hence the foot 14 is abducted about the axis of the sub-talar joint 50.

The extent of abduction achieved is determined by a number of factors including the condition of the user, the strength of the bias member 100 and the position of the restrictors 102. For clarity the second adjuster 64 is not shown in FIG. 4A, but a skilled practitioner will realise that since the leg attachment 72 extends beyond the rear centreline of the leg the foot can also be dorsiflexed about the anatomical axis of the tibio-talar joint 44.

An advantage of the configuration illustrated at in FIG. 4A is that the leg attachment 72 acts like a sling that is being pulled from either side by the first connecting arm 58 and the straps 112. The leg attachment may therefore be produced from relatively soft and flexible materials making it more comfortable for the user. The skilled practitioner will also realise that the configuration may be reversed to adduct and or plantaflex the foot.

FIG. 4B is a simplified plan view of the device 56 in use with a suitable shoe 86, the shoe 86 is closely fitting yet allows full and free movement of both sub-talar and tibio-talar joints. Providing the leg 12 is stabilised movement of the shoe 86 will correspond to movement of the foot 14. The arrangement of the first and second adjusters 66, 64 and first and second connecting arms 58, 62 means the foot may move only according to the dominant anatomical axes of the sub-talar joint 50 and tibio-talar joint 44.

In FIG. 4B the leg 12 is sectioned along the axis E-E as illustrated in FIG. 4D. FIG. 4B illustrates a right foot. The first connecting arm 58 is positioned medially. In this example the first adjuster 66 is subject to a torsion force due to the effect of the bias member 100. The effect of the torsion force is to subject the first connecting arm 58 to a force F. The force F is transferred to the leg attachment 72 such that it exerts a first bracing force F on the leg 12.

The position of the force F is further illustrated in FIG. 4D where it can be seen that a turning moment M is applied through the axis of the sub-talar joint 50. Since the leg attachment 72 cannot move and acts as a brace stabilising the leg 12 relative to the foot 14, the net effect is that the shoe 86 and hence the foot 14 is abducted about the axis of the sub-talar joint 50.

The extent of abduction achieved is determined by a number of factors including the condition of the user, the strength of the bias member 100 and the position of the restrictors 102. For clarity the second adjuster 64 is not shown in FIG. 4B, but a skilled practitioner will realise that since the leg attachment 72 extends beyond the rear centreline of the leg the foot can also be dorsiflexed about the anatomical axis of the tibio-talar joint 44.

An advantage of the configuration illustrated in FIG. 4B is that the leg attachment 72 can be relatively small providing that is made from a relatively rigid material. The skilled practitioner will also realise that the configuration may be reversed to adduct and or plantaflex the foot.

FIG. 4C is a simplified plan view of the device 56 in use with a suitable shoe 86, the shoe 86 is closely fitting yet allows full and free movement of both sub-talar and tibio-talar joints. Providing the leg 12 is stabilised movement of the shoe 86 will correspond to movement of the foot 14. The arrangement of the first and second adjusters 66, 64 and first and second connecting arms 58, 62 means the foot may move only according to the dominant anatomical axes of the sub-talar joint 50 and tibio-talar joint 44.

In FIG. 4C the leg 12 is sectioned along the axis E-E as illustrated in FIG. 4d. FIG. 4c illustrates a right foot. The first connecting arm 58 is positioned posteriorly. In this example the first adjuster 66 is subject to a torsion force due to the effect of the bias member 100. The effect of the torsion force is to subject the first connecting arm 58 to a bracing force F1. The first connecting arm 58 is attached to a rigid leg attachment 72. The force F1 is transferred through rigid the leg attachment 72 such that it exerts a first bracing force F2 on the leg 12.

The position of the force F2 is further illustrated in FIG. 4D where it can be seen that a turning moment M is applied through the axis of the sub-talar joint 50. Since the leg attachment 72 cannot move and acts as a brace stabilising the leg 12 relative to the foot 14, the net effect is that the shoe 86 and hence the foot 14 is abducted about the axis of the sub-talar joint 50.

The extent of abduction achieved is determined by a number of factors including the condition of the user, the strength of the bias member 100 and the position of the restrictors 102. For clarity the second adjuster 64 is not shown in FIG. 4c, but a skilled practitioner will realise that since the leg attachment 72 extends beyond the rear centreline of the leg the foot can also be dorsiflexed about the anatomical axis of the tibio-talar joint 44.

An advantage of the configuration illustrated at 4C is that the first connecting arm 58 is positioned conveniently to the rear of the user's leg. The skilled practitioner will also realise that the configuration may be reversed to adduct and or plantaflex the foot.

Similarly, the second bias member 100 of the second adjuster 64 provides a second bracing force which is a torsional force around the second device axis 144. Thus, the first adjuster 66 includes first biasing means for providing a first bracing force and the second adjuster includes second biasing means for providing a second bracing force which, in use, together and simultaneously brace the user's foot in any one or any suitable combination of a neutral position, an abducted position, an adducted position, a dorsiflexed position and/or a plantarflexed position.

The device 56 may include an adjustable leg attachment mounting 78 for mounting the first connecting arm 58 and the leg attachment 72 together. The adjustable leg attachment mounting 78 comprises a plurality of holes 80 defined by the first connecting arm 58. The leg attachment 72 slidably locates within a channel 82 defined by the relatively rigid outer member 74 of the leg attachment 72 and is held in a selected position by a fastener 84 such as a screw, bolt or rivet which extends through one of the holes 80 into a threaded hole (not shown defined by the relatively rigid outer member 74 of the leg attachment 72. The adjustable leg attachment mounting 78 permits linear adjustment of the leg attachment 72 relative to the first connecting arm 58.

The device 56 includes a plurality of pairs of securing straps 112 which extend from the brace part 72. The securing straps 112 could be in any convenient form, for example, in the form of laces or, as shown in FIG. 4, in the form of straps. The device 56 further includes fasteners 114 to fasten the respective straps 112 together. The fasteners 114 could be in any convenient form, for example, in the form of buckles, laces or, as shown in FIG. 4, hook and loop fastenings. The straps 112 and fasteners 114 are shown only in FIG. 4 for the sake of ease of interpretation of the drawings, but it will be understood would actually be present in the other views of the embodiment, and in other similar embodiments. It will be further understood that typically the shoe 86 would require additional straps, especially in the hind foot and midfoot area to secure the heel to the shoe in the correct position. For clarity the shoe 86 in FIG. 4 illustrates just a single strap. In other examples, the number of securing members 112 and the means of attachment of the securing members to the brace part 72 and the shoe 86 could be different.

In use, the leg attachment 72, shoe engaging item 60, first connecting arm 58, second connecting arm 68 and shoe 86 could be provided of different sizes. Prior to fitting, measurements could be taken of the leg 12 and foot 14 and appropriately sized parts selected. In one example, the parts are provided separately and assembled for fitting. In another example, the device 56 is provided pre assembled in a number of different size combinations, and the most suitable combination selected. The orthopaedic device 56 is fitted to a lower limb 110 of a user so that a leg 12 is received by the brace part 72 and a foot 14 is received by the shoe 86. The securing members 112 are fastened together. The adjustable leg attachment mounting 78 and the shoe mounting 92 can be adjusted as described above.

Initially, during fitting in the adjustment condition, the limit stops 108 could be removed for ease of adjustment, or could be positioned in an approximate position or positioned to hold the device 56 in a neutral condition with no abduction or adduction and no dorsiflexion of plantaflexion. During the fitting, the foot 14 may be manipulated to a new position, and the limit stops 108 set to brace the foot in a restricted condition. In a restricted condition the relative movement between first connecting arm 58 and the second connecting arm 68 and the second connecting arm 68 and shoe engaging item 60 is restricted relative to the movement permitted in the adjustment condition. The restricted condition may allow no movement of the tibio-talar and sub-talar joints or more typically will allow some movement permitting the user to exercise against the torsion forces exerted by the bias members 100.

In cases where the user is suffering from varus, adduction and equinus the device 56 will typically be configured to limit varus, adduction and plantaflexion and to brace or bias the foot into a position of valgus, abduction and dorsiflexion as illustrated in FIGS. 4a to 4d. For other conditions the device may be configured to brace or bias the foot in the opposite direction.

The device 56 simultaneously corresponds with the anatomical movements of both major joints of the foot. Because the device 56 can abduct (and adduct if necessary) the foot without the need for a fixed bent knee or a rigid connecting bar between both feet it enables for the first time a dynamic brace that offers improved and more acceptable therapies for a host of foot conditions. The device 56 can be used with any suitable shoe providing it can be firmly attached to the shoe engaging item 60.

FIGS. 10 to 22 show other embodiments of the invention, many features of which are similar to those already described in relation to the embodiment of FIGS. 4 to 9. Therefore, for the sake of brevity, the following embodiments will only be described in so far as they differ from the embodiment already described. Where features are the same or similar, the same reference numerals have been used and the features will not be described again. It should be also assumed, unless stated otherwise, that the methods of use for the following embodiments are similar to that described for the above embodiment.

Figure 10:
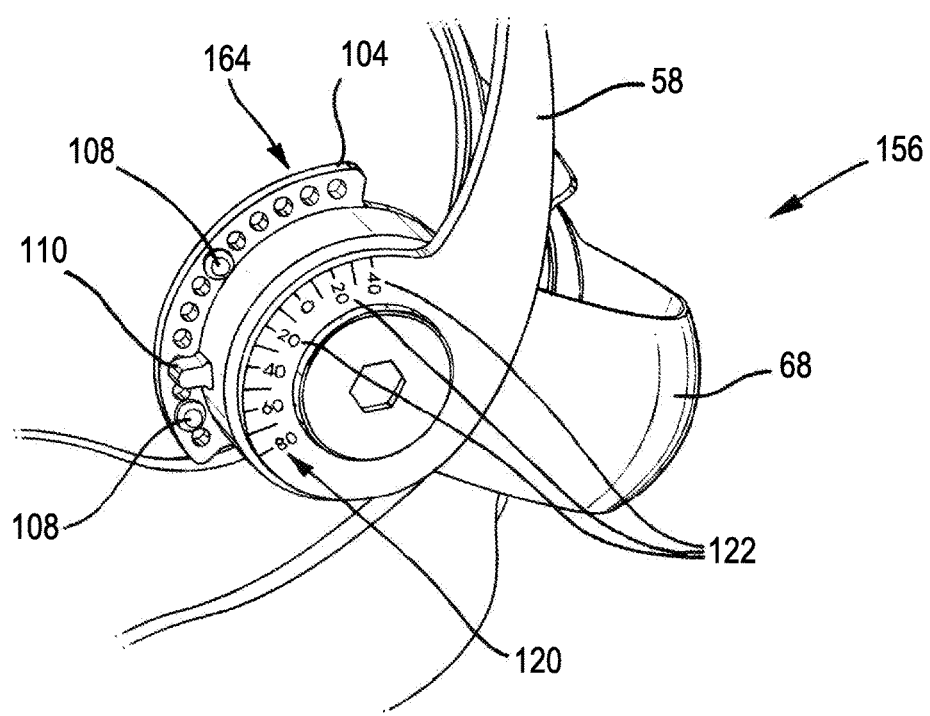
FIG. 10 is a similar view to that of FIG. 8, of a detail of a second orthopaedic device.
Figures 11, 12:
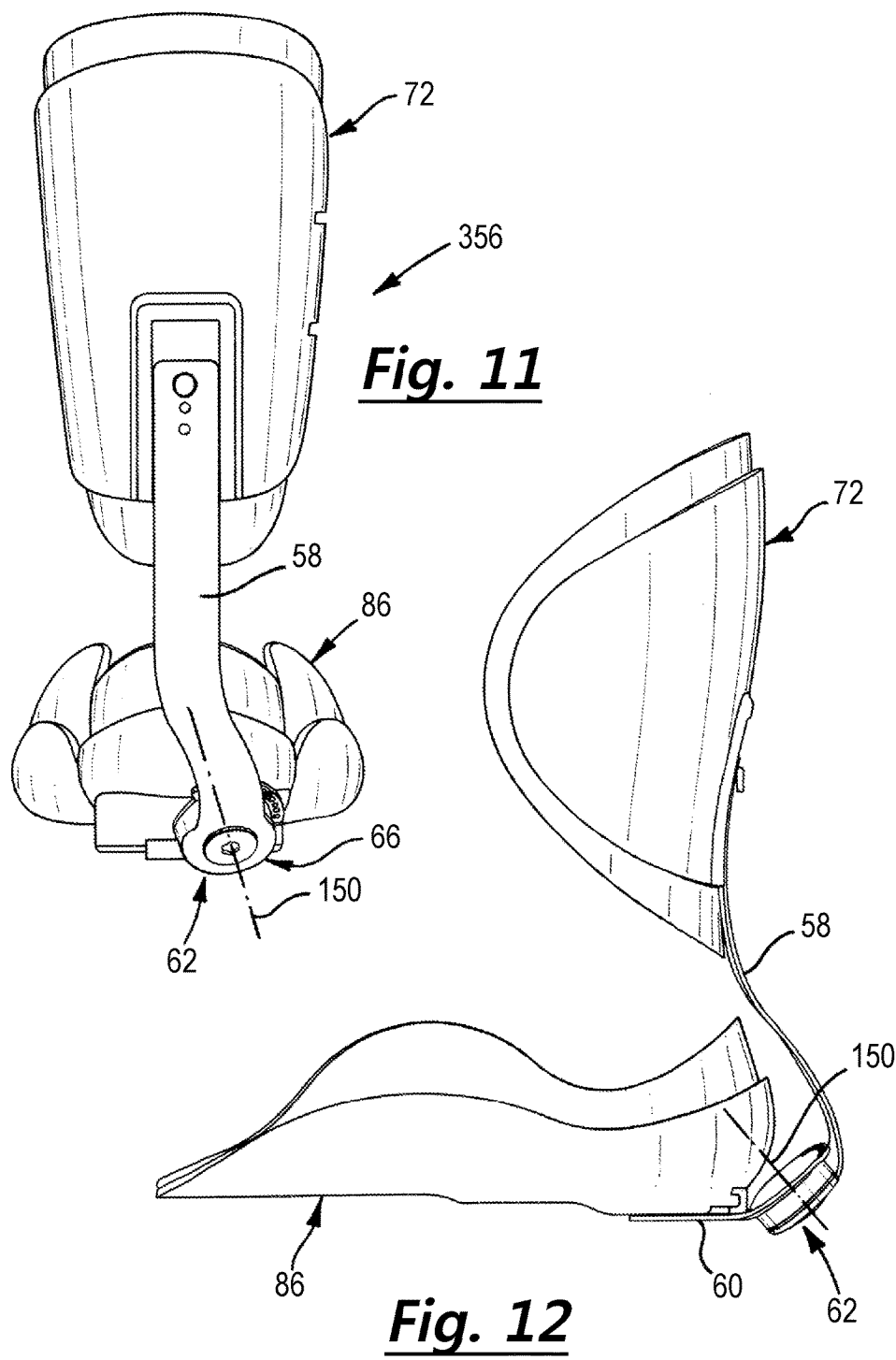
FIG. 11 is a rear view of a third orthopaedic device.
FIG. 12 is a side view of the orthopaedic device of FIG. 13.

FIG. 10 shows a detail of a second orthopaedic device 156, in which the second adjuster 164 includes an indicator 120, including a plurality of markings 122 which could indicate, for example, angles of rotation from the neutral. The first adjuster (not shown in FIG. 10) could also include an indicator 120. In the case of the second adjuster 164, the angles indicated could relate primarily to the angle of dorsiflexion or plantarflexion. In the case of the second adjuster, the angles indicated could relate primarily to the angle of inversion/adduction or eversion/abduction.

The indicator 120 permits reproducibility of setting of positions, and also enables the user and practitioner to easily monitor progress over a course of treatment, which gives encouragement and motivation. The indicator 120 can also help monitor the extent of movement during exercise as the user moves against the bias of the springs 100, again providing encouragement and motivation.

Figure 13:
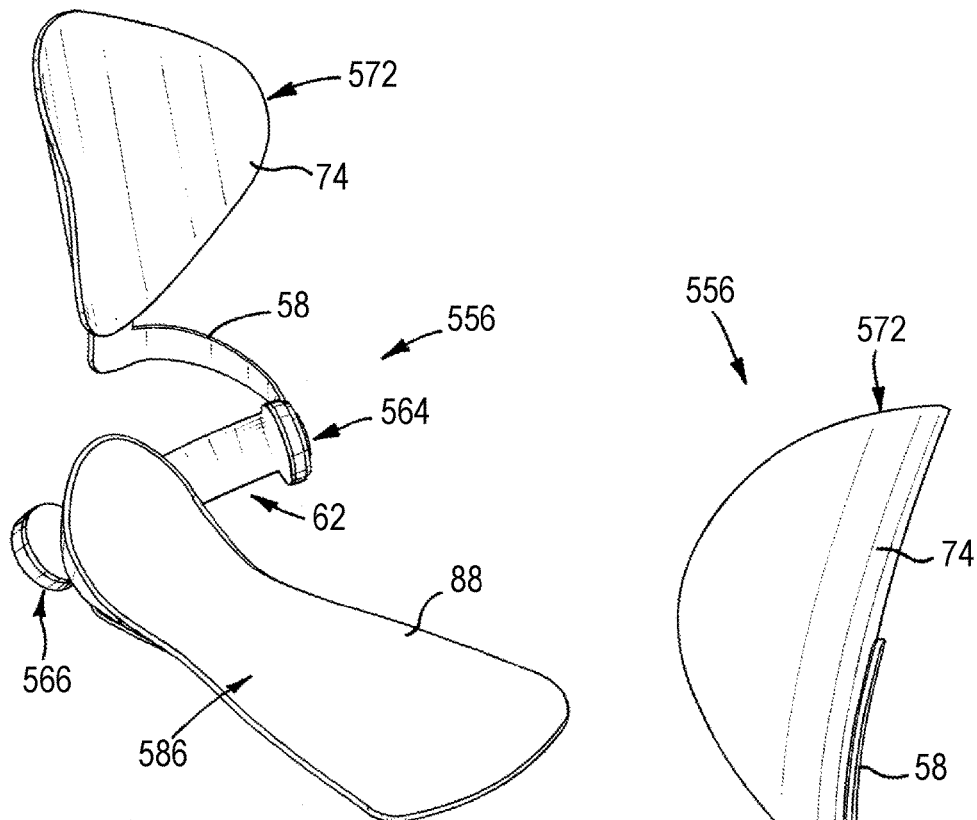
FIG. 13 is a perspective medial side view of a fourth orthopaedic device.
Figure 14:
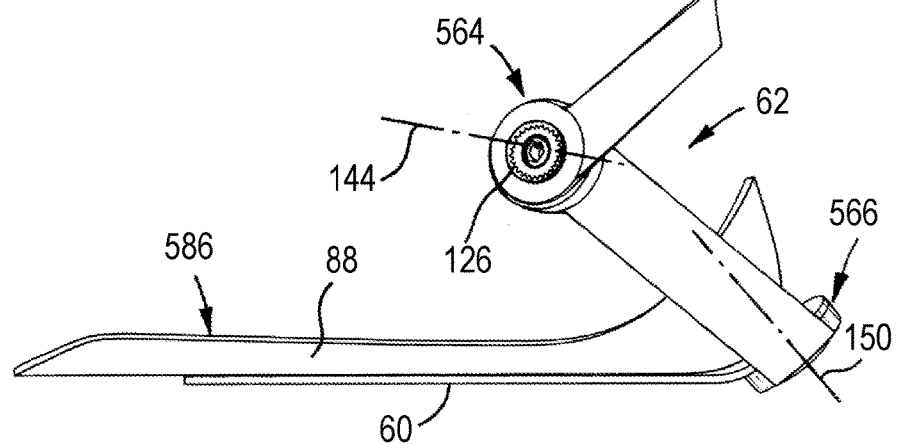
FIG. 14 is an lateral side view of the orthopaedic device of FIG. 17.
Figure 15:
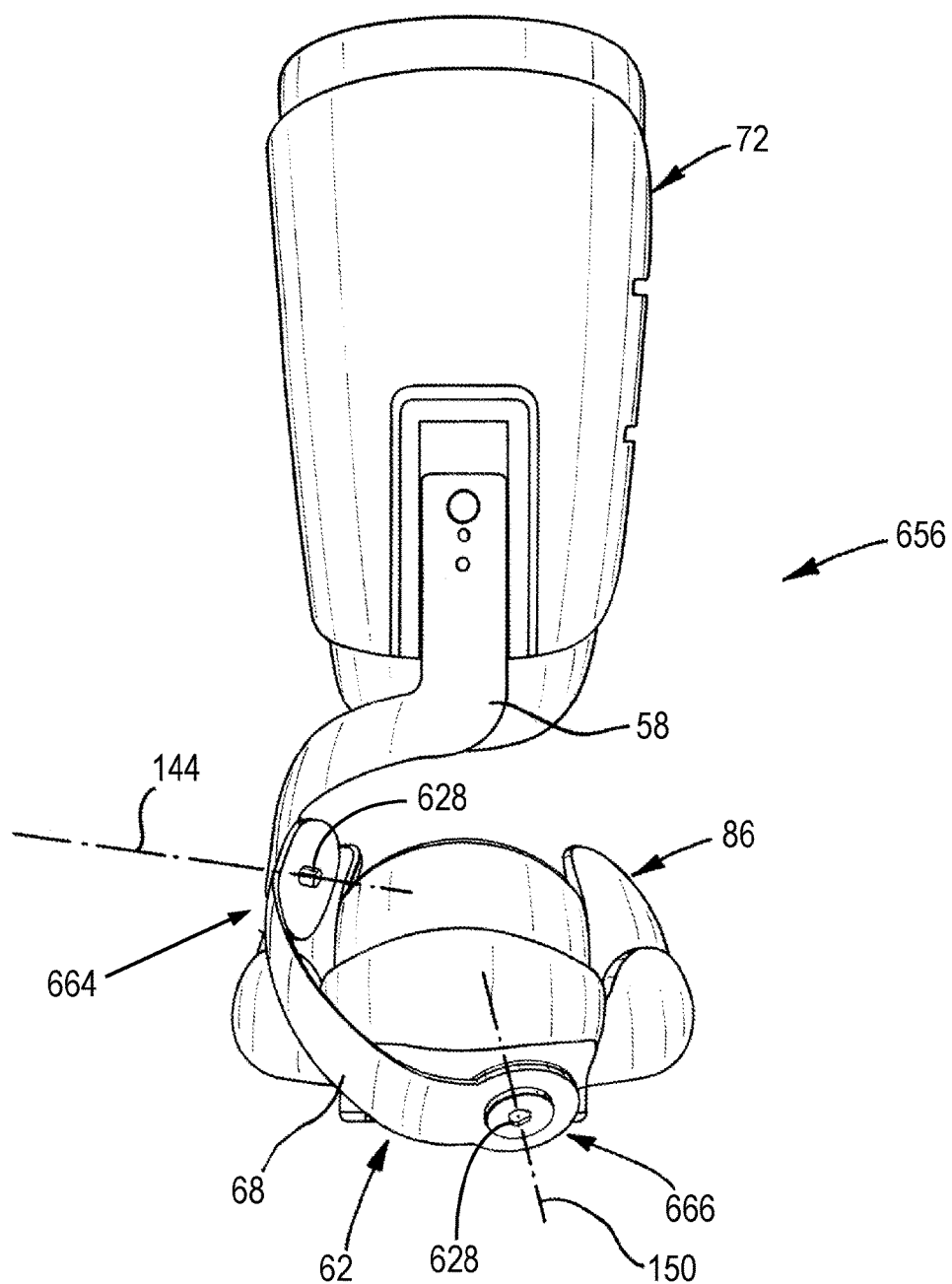
FIG. 15 is a rear view of a fifth orthopaedic device.

FIGS. 13 and 14 show a third orthopaedic device 356 including a leg engaging item 72, a first connecting arm 58 for association with a leg engaging item 72, and a shoe engaging item 60 for association with a first connecting arm 58 and shoe 86. This device has just one adjuster 66 which corresponds to the first adjuster 66 of the first embodiment. The third orthopaedic device 356 thus permits adjustment movement only about the first device axis of rotation 150, which in use in the fitted condition corresponds to the sub-talar pivot axis 50. This device 356 could be used, for example, in cases where therapy involving only movement of the foot 14 about the sub-talar pivot axis 50 is required.

Similarly, in other embodiments not shown, a device of the invention could comprise just one adjuster corresponding to the second adjuster 64 of the first embodiment.

Figure 18:
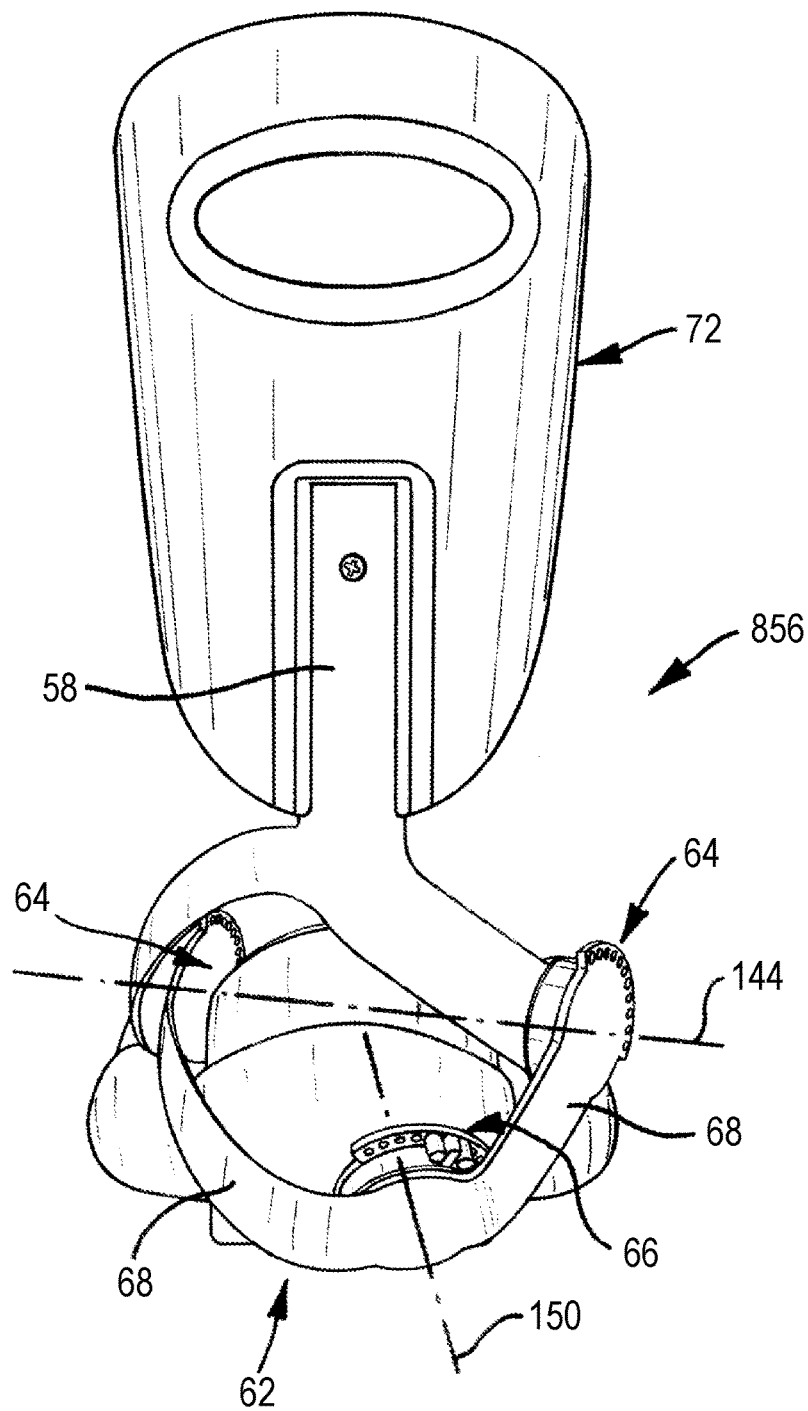
FIG. 18 is a rear view of a seventh orthopaedic device.

FIGS. 17 and 18 show a fourth orthopaedic device 556 including a leg engaging item 572, a first connecting arm 58 for association with a leg engaging item 572 and a second connecting arm 68, a second connecting arm 68 for association with a first connecting arm 58 and foot engaging item 586 including a pair of spaced adjusters 564, 566, comprising a second adjuster 564 which, in the adjustment condition, permits a second rotational adjustment movement around a second device axis of rotation 144 of the first connecting arm 58, relative to the second connecting arm 68, and a first adjuster 566, which, in the adjustment condition, permits a first rotational adjustment movement around a first device axis of rotation 150 of the second connecting arm 68 relative to the foot engaging item 586.

In this example, the leg engaging item 572 and the foot engaging item 586 are somewhat simpler than in the first embodiment, the leg engaging item 572 and foot engaging item being made of a relatively rigid, but malleable material. As with previous embodiments the first and second connecting arms 58, 62 and adjusters 566, 564 are made of a light, but rigid material. The adjusters 564, 566 are also somewhat simpler than previously described, and could, in one example, comprise a ratchet mechanism 126 which, for each adjuster, permits adjustment in one direction only.

Treatment of certain conditions of the foot especially congenital conditions in babies and young children may necessitate encasement of the lower limb 10 in a cast to immobilise it in a prescribed state of abduction or adduction and dorsiflexion or plantaflexion. It can be difficult to apply the cast while maintaining the foot 14 in the desired position, and often requires the attention of several experienced medical practitioners. Moreover, plaster casts can be prone to slippage if not perfectly formed. For this embodiment, in use, the foot is located on the foot engaging item 586 and leg engaging item 572 positioned against the lower leg. The foot is then manipulated into the desired position. The leg and foot engaging items 572 and 586 are moulded as required and then foot is manipulated into position. The relatively rigid connecting arms and adjusters assist with the manipulation process and the ratchet mechanisms assist with maintaining the desired manipulated position whilst bandage and casts are applied.

Using the fourth orthopaedic device 556 of the invention ensures that the correct position is maintained while the plaster is applied and reduces the risk of cast slippage thereby improving treatment efficacy and patient comfort. Using the fourth orthopaedic device 556 as a splint enables plaster casting to be undertaken more consistently by less experienced practitioners. The ratchet mechanism 126 makes adjustment simple and quick. The fourth orthopaedic device 556 thus provides an adjustable, disposable splint which aids the casting of the foot and leg to hold the sub-talar and tibio-talar joints is precisely manipulated condition.

FIG. 19 shows a fifth orthopaedic device 656 including a leg engaging item 72, a first connecting arm 58 for association with a leg engaging item 72 and a second connecting arm 68, a second connecting arm 68 for association with a first connecting arm 58 and a shoe engaging item 60 (not shown in FIG. 19) and a pair of spaced adjusters 664, 666, comprising a second adjuster 664 which, in the adjustment condition, permits a second rotational adjustment movement around a second device axis of rotation 144 of the first connecting arm 58 relative to the second connecting arm 68 and a first adjuster 666, which, in the adjustment condition, permits a first rotational adjustment movement around a first device axis of rotation 150 of second connecting arm 68 relative to the shoe engaging item 60.

In this example, the adjusters 664, 666 are somewhat simpler than previously described, and could, in one example, each comprise a fastener 628 which forms the respective pivot axis 144, 150. The fastener 628 could be in the form of a bolt or screw, which can be loosened or tightened to move the respective adjuster 664, 666 to the adjustment condition or the restricted condition respectively. In the restricted condition, the respective adjuster 664, 666 is substantially fixed in position.

FIGS. 20 and 21 show an sixth orthopaedic device 756 including a leg engaging item 72, a first connecting arm 58 for association with a leg engaging item 72 and a second connecting arm 68, a second connecting arm 68 for association with a first connecting arm 58 and a shoe engaging item 60 (not shown in FIGS. 20 and 21) and a pair of spaced adjusters 64, 66, comprising a second adjuster 64 which, in the adjustment condition, permits a second rotational adjustment movement around a second device axis of rotation 144 of the first connecting arm 58 relative to the second connecting arm 68 and a first adjuster 66, which, in the adjustment condition, permits a first rotational adjustment movement around a first device axis of rotation 150 of second connecting arm 68 relative to the shoe engaging item 60.

In this example, the device 756 is similar to the first device embodiment 56 except that the second connecting arm 68 extends outwardly laterally from the first adjuster 66 to the second adjuster 64, which is in a lateral position. In this position, advantageously, walking could be easier for the user as the first adjusters 64 of the two devices 756 on the two lower limbs do not dash or obstruct.

FIG. 22 shows a seventh orthopaedic device 856 including a leg engaging item 72, a first connecting arm 58 for association with a leg engaging item 72 and a second connecting arm 68, a second connecting arm 68 for association with a first connecting arm 58 and a shoe engaging item 60 (not shown in FIG. 22) and three spaced adjusters 64, 66, comprising a pair of second adjusters 64 which, in the adjustment condition, permits a second rotational adjustment movement around a second device axis of rotation 144 of the first connecting arm 58 relative to the second connecting arm 68 and a first adjuster 66, which, in the adjustment condition, permits a first rotational adjustment movement around a first device axis of rotation 150 of second connecting arm 68 relative to the shoe engaging item 60.

One of the pair of spaced second adjusters 64 is positioned on the medial side and the other is positioned on the lateral side. The second connecting arm 68 includes a spacer member 68 which extends medially from the second adjuster 66 to the medial second adjuster 64 and another spacer member 68 which extends laterally from the first adjuster 66 to the lateral second adjuster 64. The pair of second adjusters 64 provides additional strength to the device 856.

Various other modifications could be made without departing from the scope of the invention. The orthopaedic device and the various components thereof could be of any suitable size and shape, and could be formed of any suitable material(s). The adjusters could be provided in any suitable way, and could be different to those described. The biasing could be provided in a different way. For example, elastic straps or bands could provide the biasing.

Any of the features of any of the embodiments shown or described could be combined in any suitable way, within the scope of the overall disclosure of this document.

There is thus provided an orthopaedic device which simultaneously corresponds with the anatomical movements of both major joints of the foot. The device can abduct (and adduct if necessary) the foot without the need for a fixed bent knee or a rigid connecting bar between both feet. It enables for the first time a dynamic brace that offers improved and more acceptable therapies for a host of foot conditions. Many of the problems associated with conventional orthopaedic devices have thus been overcome.

Compared with prior art foot abduction (or adduction) braces based on the connecting bar concept the device enables the user to walk and run normally and thus can be used for daytime as well as night-time therapy; functionality is not compromised by rotation of the hips and knees; the device does not stress hips and knees; the device can be used unilaterally; the device is less obtrusive and more acceptable to parents and patients; the device enables more precise therapy and measurement of progress; the device can simultaneously provide therapy to both the sub-talar and tibio-talar joints.

Compared with prior art foot abduction (or adduction) braces based on the fixed bent knee concept the device enables the user to walk and run normally and thus can be used for daytime as well as night-time therapy; the device enables the leg to move and for muscles to be developed or maintained and does not compromise muscle development; the device is less obtrusive and more acceptable to parents and patients; the device enables more precise therapy and measurement of progress; the device can simultaneously provide therapy to both the sub-talar and tibio-talar joints.

Compared with prior art foot drop braces and other general purpose Ankle Foot Orthosis (AFOs) the device enables the user to walk and run with an improved and more normal gait as it simultaneously supports anatomically correct motion of tibio-talar and sub-talar joints; the device can simultaneously provide therapy to both the sub-talar and tibio-talar joints.

The invention claimed is:

1. An ankle foot orthopaedic device, the device including a first part for association with a leg engaging item, a second part for association with a foot engaging item, a connector for connecting the first part to the second part, the connector including a first adjuster, which, in an adjustment condition, permits a first adjustment relative movement of the first part and the second part around a first device axis of rotation, the connector including a second adjuster, which, in an adjustment condition, permits a second adjustment relative movement of the first part and the second part around a second device axis of rotation, wherein, the device is configured, such that in use in a fitted condition in which the device is fitted to a user's leg and foot, the first device axis is adapted to substantially correspond with a dominant anatomical axis of rotation of the sub talar joint and the second device axis is adapted to substantially correspond with a dominant anatomical axis of rotation of the tibio-talar joint, wherein, the first device axis of rotation of the first adjuster subtends a first device angle to the transverse plane in the sagittal plane extending posterior plantar to anterior dorsal, and subtends a second device angle to the sagittal plane in the transverse plane extending posterior lateral to anterior medial, wherein, the second device axis of rotation of the second adjuster subtends a third device angle to the frontal plane in the transverse plane extending medial anterior to lateral posterior, and subtends a fourth device angle to the transverse plane in the frontal plane extending medial dorsal to lateral plantar, wherein, in a neutral condition in which a sole of the user's foot is substantially at 90° to the user's leg:

the first device angle lies in the range 37° to 47°;
the second device angle lies in the range 12° to 20°;
the third device angle lies in the range 15° to 35°; and
the fourth device angle lies in the range 6° to 10°.

2. The device according to claim 1, in which, when the device is fitted to a user's leg and foot the first and second device axes are configured to be substantially aligned along the sub-talar joint axis and the tibio-talar joint axis respectively.

3. The device according to claim 1, in which the first adjuster includes a first bias member for providing a first bracing force for bracing, in use, a user's sub talar joint in an abducted, neutral or adducted position.

4. The device according to claim 1, in which the first adjuster includes a first bias member for providing a first bracing force for bracing, in use, a user's sub talar joint in an abducted, neutral or adducted position and the first bracing force is a torsion force.

5. The device according to claim 1, in which the second adjuster includes a second bias member for providing a second bracing force for bracing, in use, a user's tibio talar joint in a dorsiflexed, neutral or plantarflexed position.

6. The device according to claim 1, in which the second adjuster includes a second bias member for providing a second bracing force for bracing, in use, a user's tibio talar joint in a dorsiflexed, neutral or plantarflexed position and the second bracing force is a torsion force.

7. The device according to claim 1, in which the first adjuster includes a first bias member for providing a first bracing force and the second adjuster includes a second bias member for providing a second bracing force which, in use, together and simultaneously brace the user's foot in any one or any suitable combination of a neutral position, an abducted position, an adducted position, a dorsiflexed position and/or a plantarflexed position.

8. The device according to claim 1, in which each or any one adjuster includes an indicator, which indicates a relative degree of the adjustment movement.

9. The device according to claim 1, in which the device is moveable to a fitted, braced condition, the device being configured to hold the user's foot in any one or any suitable combination of a neutral position, an abducted position, an adducted position, a dorsiflexed position and/or a plantarflexed position, without the need for a connecting bar extending between the user's feet, or the leg engaging item extending above the user's knee, or the user's leg being held in a bent position.

10. The device according to claim 1, in which the device includes the leg engaging item, which comprises a brace part, in which a leg part of the lower limb is receivable.

11. The device according to claim 1, in which the device includes the foot engaging item, which comprises a shoe or footplate, in which a foot part of the lower limb is receivable.

12. A splint for aiding immobilization of a body part including an ankle foot orthopaedic device according to claim 1.

13. The device according to claim 1, the third device angle lies in the range 20° to 30°.

14. The device according to claim 1, the first device angle is 42°.

15. The device according to claim 1, wherein the second device angle is 16°.

16. The device according to claim 1, wherein the third device angle is 25°.

17. The device according to claim 1, wherein the fourth device angle is 8°.

* * * * *